United States Patent
Chen

(10) Patent No.: US 9,603,389 B2
(45) Date of Patent: Mar. 28, 2017

(54) ELECTRONIC CIGARETTE

(71) Applicant: SHENZHEN SMOORE TECHNOLOGY LIMITED, Shenzhen (CN)

(72) Inventor: Zhiping Chen, Shenzhen (CN)

(73) Assignee: Shenzhen Smoore Technology Limited, Shenzhen (CN)

( * ) Notice: Subject to any disclaimer, the term of this patent is extended or adjusted under 35 U.S.C. 154(b) by 471 days.

(21) Appl. No.: 14/144,718

(22) Filed: Dec. 31, 2013

(65) Prior Publication Data

US 2015/0090279 A1    Apr. 2, 2015

(30) Foreign Application Priority Data

Sep. 29, 2013  (CN) .......................... 2013 1 0459597

(51) Int. Cl.
*A24F 47/00* (2006.01)
*A61M 15/06* (2006.01)

(52) U.S. Cl.
CPC ........... *A24F 47/008* (2013.01); *A61M 15/06* (2013.01)

(58) Field of Classification Search
CPC ....... A61M 15/06; A24F 47/00; A24F 47/002; A24F 47/004; A24F 47/008
See application file for complete search history.

(56) References Cited

U.S. PATENT DOCUMENTS

| | | | |
|---|---|---|---|
| 2011/0155718 A1* | 6/2011 | Greim | F24H 1/0018 219/507 |
| 2013/0037041 A1* | 2/2013 | Worm | A24F 47/008 131/329 |
| 2013/0340750 A1* | 12/2013 | Thorens | A24F 47/008 128/202.21 |
| 2014/0318559 A1 | 10/2014 | Thorens et al. | |
| 2015/0027455 A1* | 1/2015 | Peleg | A24F 47/008 131/328 |
| 2015/0164143 A1* | 6/2015 | Maas | A24F 47/008 131/329 |

FOREIGN PATENT DOCUMENTS

| | | |
|---|---|---|
| CN | 102014677 A | 4/2011 |
| CN | 203068713 U | 7/2013 |

* cited by examiner

*Primary Examiner* — Anthony Calandra
(74) *Attorney, Agent, or Firm* — Coats & Bennett, PLLC

(57) ABSTRACT

An electronic cigarette is provided, which includes: a housing, a liquid reservoir, and an atomizer assembly. The housing has a chimney formed therein; the liquid reservoir is used for storing liquid; the atomizer assembly received in the housing. The atomizer assembly includes a heating plate capable of absorbing liquid. An outer surface of the heating plate is in contact with the air in the chimney.

15 Claims, 3 Drawing Sheets

ELECTRONIC CIGARETTE

FIELD OF THE INVENTION

The present disclosure relates to an electronic cigarette.

BACKGROUND OF THE INVENTION

The electronic cigarette is also known as a virtual cigarette or an electronic atomizer. As a replacement for cigarette, the electronic cigarette is usually used for smoking cessation. The appearance and taste of electronic cigarette are similar to that of the conventional cigarette, while it does not contain tar, suspended particles and other harmful ingredients as the conventional cigarette.

The electronic cigarette is mainly composed of an atomizer and a battery assembly. The atomizer is the core device of the electronic cigarette for generating atomizing gas; the quality and taste of the smoke are dependent on the atomization effect. A conventional heating element of the atomizer can only heat and atomize the liquid located close to the heating wire. As such the atomization effect of the liquid located away from the heating wire is poor. Or even if the liquid can be atomized, the atomized particles are relatively large due to the low atomization temperature.

SUMMARY OF THE DISCLOSURE

This section provides a general summary of the disclosure, and is not a comprehensive disclosure of its full scope or all of its features.

The present disclosure is directed to an electronic cigarette having a better atomization effect.

An electronic cigarette includes a housing having a chimney formed therein; a liquid reservoir received in the housing; and an atomizer assembly received in the housing, the atomizer assembly includes a heating plate capable of absorbing liquid, an outer surface of the heating plate is in contact with an air in the chimney.

In one embodiment, the housing has a receiving cavity for receiving various internal components of the electronic cigarette, such as the atomizer assembly and the liquid reservoir. The housing defines an air inlet and an air outlet; accordingly, the air can enter the housing and go out the chimney with the atomized gas during use.

In one embodiment, the liquid reservoir is a component mainly used for storing liquid. In one embodiment, the liquid reservoir is a liquid container located in the housing but is independent from the housing. Alternatively, it can also be a container with an opening formed by surrounding of a part of the wall of the housing. Or it can be made from fibers, blankets, temperature resistance and non-toxic sponges, and other materials with great capacity of absorbing liquid, such that the liquid can be filled or stored in the liquid reservoir. Further, the shape of the liquid reservoir is adapted to that of the housing, such as rectangular cylinder or cylinder and so on. In addition, the liquid reservoir can be configured in any position of the receiving cavity of the housing, such as in the center or close to one side of the receiving cavity, as long as the chimney is not blocked by the liquid reservoir.

In one embodiment, the chimney can be located in the center of the housing, or close to one side of the housing. When the chimney is located close to the side of the housing, at least partial wall of the chimney is integrally formed with the wall of the liquid reservoir. The chimney is connected to the air inlet and the air outlet, respectively; accordingly, the atomized particles generated by the atomizer assembly can pass through the chimney and go out of the housing.

The liquid can be atomized by the atomizer assembly to form atomizing gas for users to inhale. The atomizer assembly includes at least a heating plate capable of absorbing liquid.

In one embodiment, the heating plate is plate-shaped, which is a heating element with a capacity of directly absorbing liquid, and allowing the liquid to be uniformly distributed on the heating plate. The heating plate can be directly in contact with the liquid reservoir, or it can be in contact with the liquid reservoir with a help of other components, such as a liquid conductor. One end of the liquid conductor is connected to the liquid reservoir, and the other end of the liquid conductor is connected to the heating plate, and the liquid stored in the liquid reservoir can be transferred to the heating plate by the liquid reservoir.

The heating plate is plate-shaped, which does not mean that the surface of the heating plate is flat, it can be plate-like with a curvature, accordingly, the heating plate has a much greater surface to heat and absorb liquid.

Alternatively, the heating plate can be configured with other structures.

For example, in one embodiment, the heating plate includes a plate-shaped substrate and a heating film covered on the substrate. Further, the heating film is positive temperature coefficient (PTC) film or a conductive heating coating layer, the substrate is made of microporous material. The PTC film is a membranous heating wire coated on the surface of the substrate. Accordingly, the whole heating plate can heat when the PTC film or conductive heating coating layer is heating, and the liquid absorbed by the heating plate can be atomized when the heating plate is passively heated.

In an alternative embodiment, the heating plate includes a plate-shaped substrate and a heater close to an outer surface of the substrate. Accordingly, when the heater is heating, the heat can be directly transferred to the whole heating plate, and the liquid absorbed by the heating plate can be atomized when the heating plate is passively heated.

In an alternative embodiment, the heating plate is made of foamed metal, foamed graphite or porous ceramic. And the liquid absorbed by the heating plate can be atomized when the heating plate is active heating.

At least partial surface of the heating plate is in contact with the air in the chimney, it means that at least partial surface of the heating plate is exposed to the air in the chimney. Accordingly, the liquid can be atomized by the heating plate and then diffused to the air in the chimney, and the flowing air brings it out of the chimney.

Compared to the prior art, the foregoing technical solution has the following advantages:

Since the heating plate is plate-shaped, the heating plate has much greater surface area to heat and absorb liquid. The liquid absorbed by the heating plate can be diffused on the entire surface thereof and forms a heated liquid layer with a uniform thickness, and the whole liquid layer can be heated by the heating plate to generate uniformly atomized particles, accordingly, the atomization effect is excellent. In addition, the fabrication process of the heating plate is relatively simple, and there is no need to twine a heating wire around a fixed axis; accordingly, the assembly operation is simplified.

Further, the heating plate defines a ventage for air circulating. The ventage forms a portion of the chimney. The atomized particles on the upper surface or the lower surface can be brought out when the air passes through the ventage. Better air circulation is provided due to the ventage.

Further, the outer wall of the heating plate and the chimney defines an air space for air circulating therebetween.

The heating plate is disposed in the chimney but does not block the chimney. The air entered from the air inlet can freely flow through the chimney and go out from the outlet. The user can easily inhale the smoke. Moreover, the pressure in the chimney is much smaller than that of the liquid reservoir; accordingly, the liquid can be easily absorbed by the heating plate.

Further, the heating plate defines a plurality of micropores. The micropores penetrate through the heating plate; alternatively, the micropores do not penetrate through the heating plate. There are 1200 to 4900 micropores per square centimeter on the heating plate, accordingly, the surface area of the heating plate is enlarged, and the storing capacity of the heating tube is improved. The liquid is uniformly distributed on the heating plate. Further, the heating area of the heating plate is also enlarged; the speed of the atomization is enhanced.

Further, the heating plate defines a plurality of micropores. The micropores are penetrated through the heating plate, a surface of the heating plate is bonded to the liquid reservoir; the air in the chimney is capable of blowing the other surface of the heating plate. Accordingly, the liquid absorbed by one surface of the heating plate passes through the micropores to the other surface, then is atomized when the heating plate is heated. The wall of the heating plate and the wall of the liquid reservoir are bonded to each other to form a face to face contact; a large amount of liquid can be quickly absorbed by the heating plate and uniformly distributed on the heating plate. The atomized gas on the surface of the heating plate is capable of diffusing to the air in the chimney.

Further, the electronic cigarette includes a liquid conductor, one end of the liquid conductor is connected to the liquid reservoir, and the other end is connected to the heating plate.

In one embodiment, the liquid conductor is made of fibers, sponges, and other material with great capacity of absorbing liquid; the liquid conductor can also be made of fine pipette. The liquid can be transported by capillary action, the phenomenon that the heating tube is directly in contact with the liquid reservoir is avoided, and the loss of a large amount of heat transferring to the liquid reservoir is reduced. Accordingly, the efficiency of the heat is greatly enhanced, and the risk that the liquid reservoir is accelerated aged because the liquid reservoir is heated for the long time by the heating tube is avoided, and the risk that the powder generated by the liquid reservoir effects the quality of the smoke is avoided, moreover, the risk of the damage of the liquid reservoir caused by the heating tube is also avoided.

Further areas of applicability will become apparent from the description provided herein. The description and specific examples in this summary are intended for purpose of illustration only and are not intended to limit the scope of the present disclosure.

BRIEF DESCRIPTION OF THE DRAWINGS

The components in the drawings are not necessarily drawn to scale, the emphasis instead being placed upon clearly illustrating the principles of the present disclosure. Moreover, in the drawings, like reference numerals designate corresponding parts throughout the views.

DETAILED DESCRIPTION OF THE EMBODIMENTS

Illustrative embodiments of the disclosure are below. The following explanation provides specific details for a thorough understanding of and enabling description for these embodiments. One skilled in the art will understand that the disclosure may be practiced without such details. In other instances, well-known structures and functions have not been shown or described in detail to avoid unnecessarily obscuring the description of the embodiments.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively. Additionally, the words "herein," "above," "below" and words of similar import, when used in this application, shall refer to this application as a whole and not to any particular portions of this application. When the claims use the word "or" in reference to a list of two or more items, that word covers all of the following interpretations of the word: any of the items in the list, all of the items in the list and any combination of the items in the list.

EXAMPLE ONE

Figure 1:
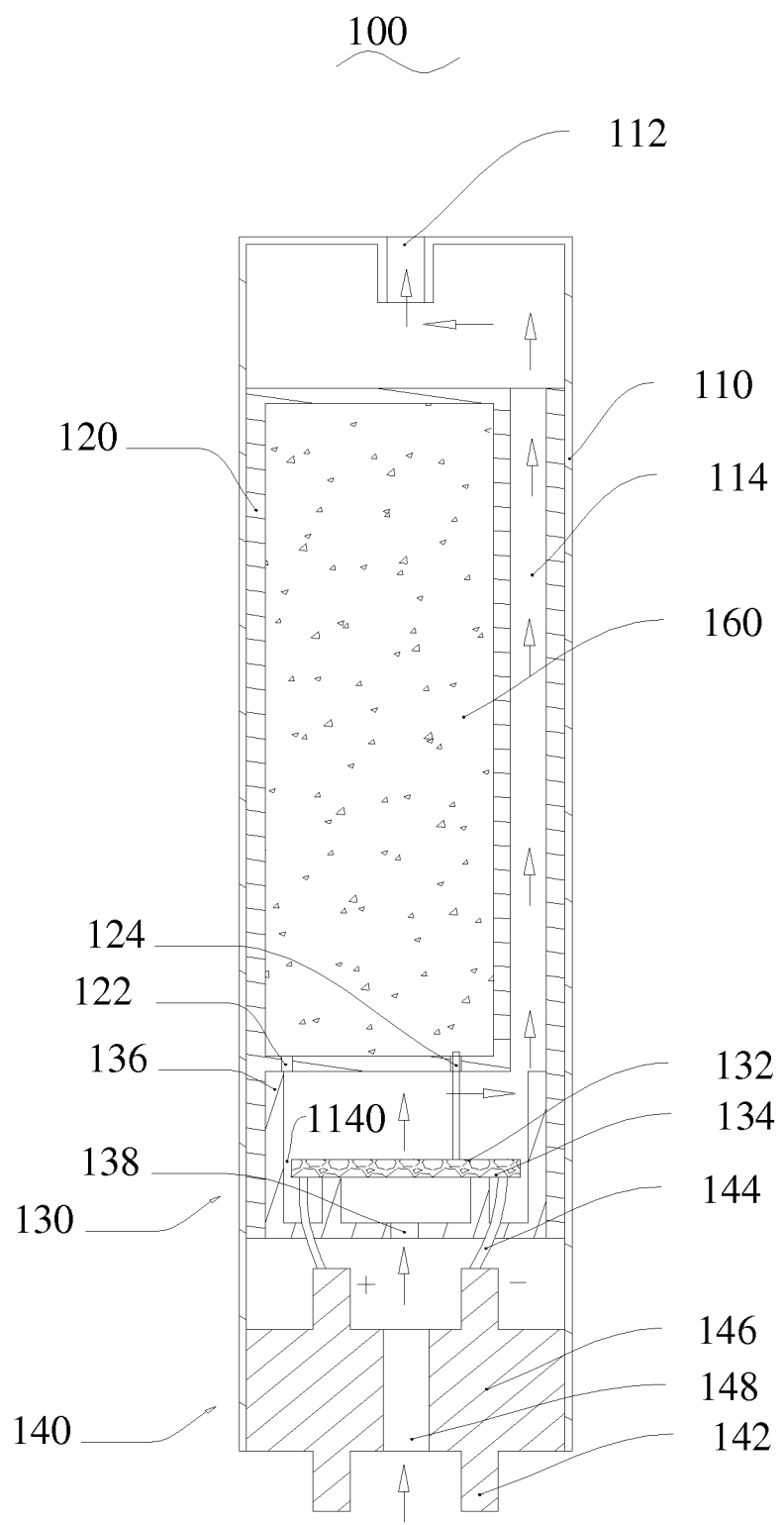
FIG. 1 is a cross-sectional view of an electronic cigarette according to a first embodiment.
Figure 2:
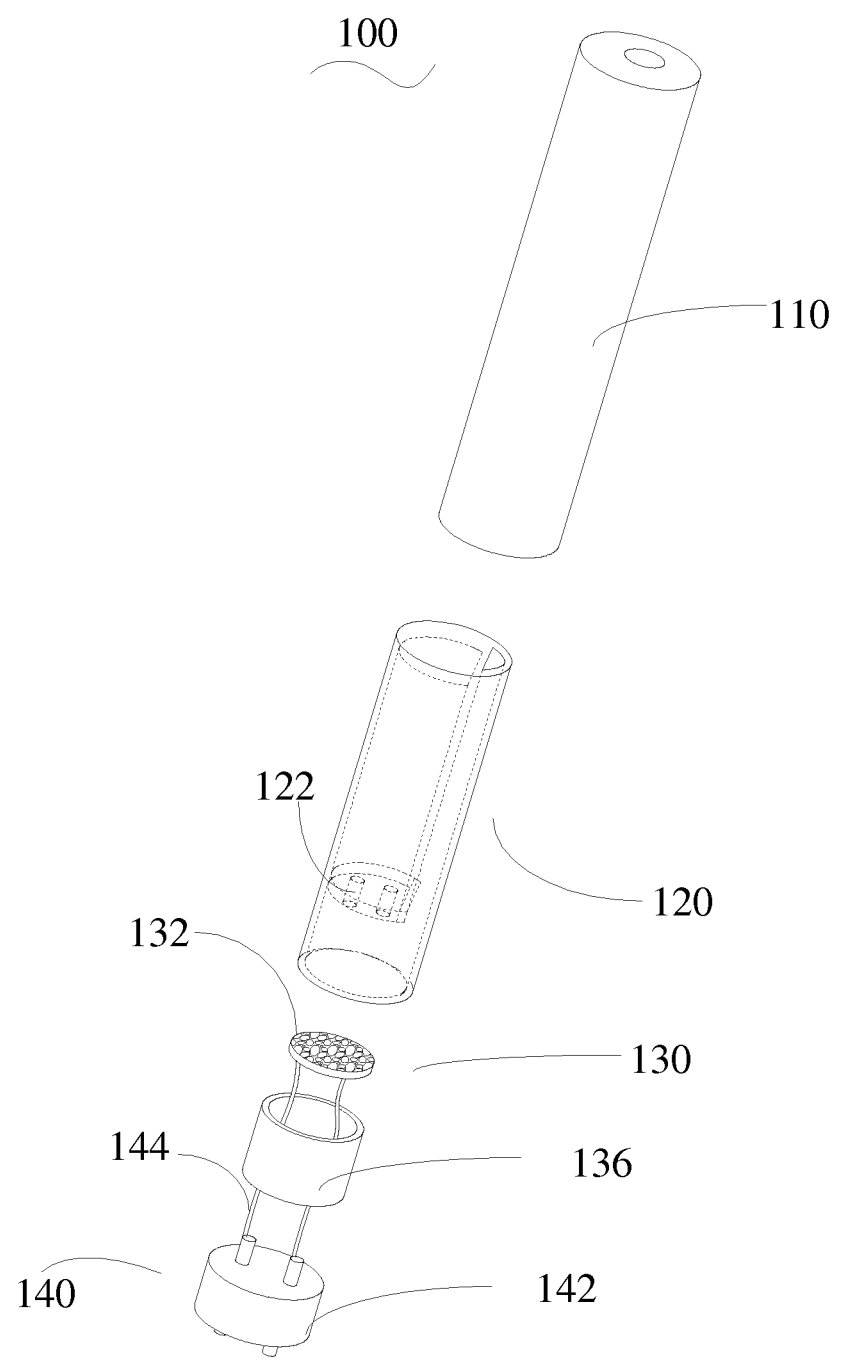
FIG. 2 is an exploded perspective view of the electronic cigarette shown in FIG. 1.

Referring to FIG. 1 and FIG. 2, a first embodiment of an electronic cigarette 100 includes a housing 110, a liquid reservoir 120, an atomizer assembly 130, and a power supply assembly 140. The liquid reservoir 120, the atomizer assembly 130, and the power supply assembly 140 are received in the housing 110. The liquid 160 stored in the liquid reservoir 120 can be transferred to the atomizer assembly 130. The power supply assembly 140 is used to supply power to the atomizer assembly 130.

The housing 110 is shaped approximately as a hollow cylinder and has a circular cross-section. The housing 110 has a cavity for receiving various internal components of the electronic cigarette 100. The housing 110 is made of plastic. In alternative embodiments, the housing 110 is a rectangular cylinder, oval cylinder and so on. The housing 110 defines an air outlet 112 on an end thereof and an air intake (not shown) on the other end thereof. The housing 110 is provided with a filter nozzle (not shown) close to the end of the air outlet 112 to filter nicotine and other chemical substances in the smoke. The housing 110 forms a chimney 114 therein to connect the air outlet 112 and the air intake. The atomized particles generated by the atomizer assembly 130 can go out of the housing 110 through the chimney 114.

In the illustrated embodiment, the liquid reservoir 120, which is used to store the liquid 160, is a sealed container formed by part of the wall of the housing 110. Alternatively, the liquid reservoir 120 is a liquid container located in the housing 110 but is independent from the housing 110. The liquid reservoir 120 is shaped approximately as a cylinder. In the illustrated embodiment, the cross section area of the liquid reservoir 120 is smaller than that of the housing 110, such that the space between the wall of the liquid reservoir 120 and the inner wall of the housing 110 forms a part of the chimney 114. Alternatively, the liquid reservoir 120 is cube or the like. The liquid reservoir 120 defines an outlet orifice 122 allowing the liquid 160 to flow out on an end thereof. The liquid 160 stored in the liquid reservoir 120 can be transferred to the atomizer assembly 130 through the outlet orifice 122. In the illustrated embodiment, two outlet orifices 122 is provided, alternatively, three or more outlet orifices 122 can be provided. The diameter of the outlet orifice 122 is approximately 0.5 mm to 2.5 mm. The number and the size of the outlet orifice 122 can be reasonable configured according to the actual demand. A suitable amount of the liquid 160 can be transferred to the atomizer assembly 130 by flowing out from the outlet orifice 122. Combined with the atomization of the atomizer assembly 130, a suitable smoke can be generated to get a better taste.

Referring to FIG. 1, in the illustrated embodiment, the atomizer assembly 130 includes a liquid conductor 124. One end of the liquid conductor 124 is connected to the liquid reservoir 120, and the other is connected to the heating plate 132. The liquid conductor 124 is made of fibers for better transferring the liquid 160 to the atomizer assembly 130.

The atomizer assembly 130 is used to atomize the liquid 160 to form atomizing gas for users to inhale. The atomizer assembly 130 is received in the housing 110 and positioned at the lower end of the liquid reservoir 120 with the outlet orifice 122. The atomizer assembly 130 includes a heating plate 132 capable of absorbing liquid. The heating plate 132 is horizontally positioned in the chimney 114 and the whole outer surface of the heating plate 132 is in contact with the air in the chimney 114; accordingly, the atomized gas generated by the heating plate 132 can diffuse to the air in the chimney 114. Further, the heating plate 132 is plate-shaped and has a larger heating area, the liquid 160 can be uniformly heated to generate uniform atomized particles, thus improving the atomization.

Referring to FIG. 1, a side wall of the heating plate 132 and a side wall of the chimney 114 defines an air space 1140 therebetween for improving the air circulation; accordingly, the air entering the chimney 114 is capable of blowing the heating plate 132. The air can freely pass through the chimney 114 and go out from the outlet 112. The user can easily inhale the smoke. Moreover, the pressure in the chimney 114 is much smaller than that of the liquid reservoir 120; accordingly, the liquid 160 can be easily absorbed by the heating plate 132.

Referring to FIG. 1, in the illustrated embodiment, the heating plate 132 is made of foam metal; the heating plate 132 is a microporous plate with 2000 to 3000 micropores per square centimeter. The heating plate 132 is an active heating element. The liquid 160 transferred by the liquid conductor 124 is free to crawl on the heating plate 132 by capillary action; then the liquid 160 is uniformly distributed on the heating plate 132 and uniformly heated. The amount of the liquid 160 absorbed by the heating plate 132 is increased due to the micropores. When the heating plate 132 is electrified to generate heat, and the liquid 160 is uniformly heated by the heating plate 132, then the liquid 160 is atomized to generate uniform particles, further improving the atomization effect. Moreover, since the heating plate 132 is not necessary to be made of fiber or the like, the risk that the powder is generated by the fiber being heated for a long time is avoided, and the smoke quality is not affected by the powder, and the security implications are avoided. Further, the fabrication process of the heating plate 132 is simple, and there is no need to twine a heating wire around the fixed axis; accordingly, the assembly operation is simplified.

Alternatively, the heating plate 132 includes a plate-shaped substrate and a heating film covered on a surface of the substrate. The heating film is a PTC film or a conductive heating coating layer. Alternatively, the heating plate 132 includes a plate-shaped substrate and a heater placed on an outer surface of the substrate. Those heating plates are passively heated, while the liquid 160 can also be uniformly absorbed and heated.

In order to prevent the user from being damaged by a large amount of heat on the housing 110 transferred from the heating plate 132, the atomizer assembly 130 includes an insulating supporter 136. The insulating supporter 136 is received in the housing 110, the heating plate 132 is fixed to the insulating supporter 136.

Referring to FIG. 1 and FIG. 2, the insulating supporter 136 is ring-shaped, the insulating supporter 136 defines an air passage 138 for air circulating on the bottom thereof. The outer wall of the insulating supporter 136 is bonded to the inner wall of the housing 110, such that it is easily installed, and the stability is excellent. The insulating supporter 136 is made of heat-resistant plastic and the like, which is insulated and heat resisted. The overheating of the housing 110 caused by the direct contact between the heating plate 132 and the housing 110 is avoided. Alternatively, the insulating supporter 136 is omitted.

Referring to FIG. 1 again, the power supply assembly 140 is received in the housing 110, and electrically connected to the heating plate 132 to supply power. In the illustrated embodiment, the power supply assembly 140 also includes an electrode 142, a wire 144, an electrode supporter 146, and battery (not shown). The electrode 142 is connected to the heating plate 132 by the wire 144. The electrode 142 is inserted into the electrode supporter 146, the electrode supporter 146 defines an air hole 148 for air circulating. Alternatively, the electrode supporter 146 is omitted.

The assembly process of the electronic cigarette 100 is described as follows: first of all, the liquid reservoir 120 is fixed in the cavity of the housing 110, and the heating plate 132 is fixed to the insulating supporter 136 to form the atomizer assembly 130; and the heating plate 132 is connected to the electrode 142 of the power supply assembly 140 by the wire 144, then the electrode 142 is inserted into the electrode supporter 146, finally, the housing 110 is sleeved to the electrode supporter 146 and the process is finished. It should be understood that the assembly sequence can be adjusted as needed.

In use, as the arrows shown in the FIG. 1, when the user inhales the electronic cigarette 100 on the end of the air outlet 112, the airflow enters the electronic cigarette 100 from the air inlet, then passes through the air hole 148 of the electrode supporter 146 and the air passage 138 of the insulating supporter 136, and passes through the micropores of the heating plate 132, then carries the atomized liquid to the chimney 114, and finally enters the mouth of the user by passing through the air outlet 112.

EXAMPLE TWO

Figure 3:
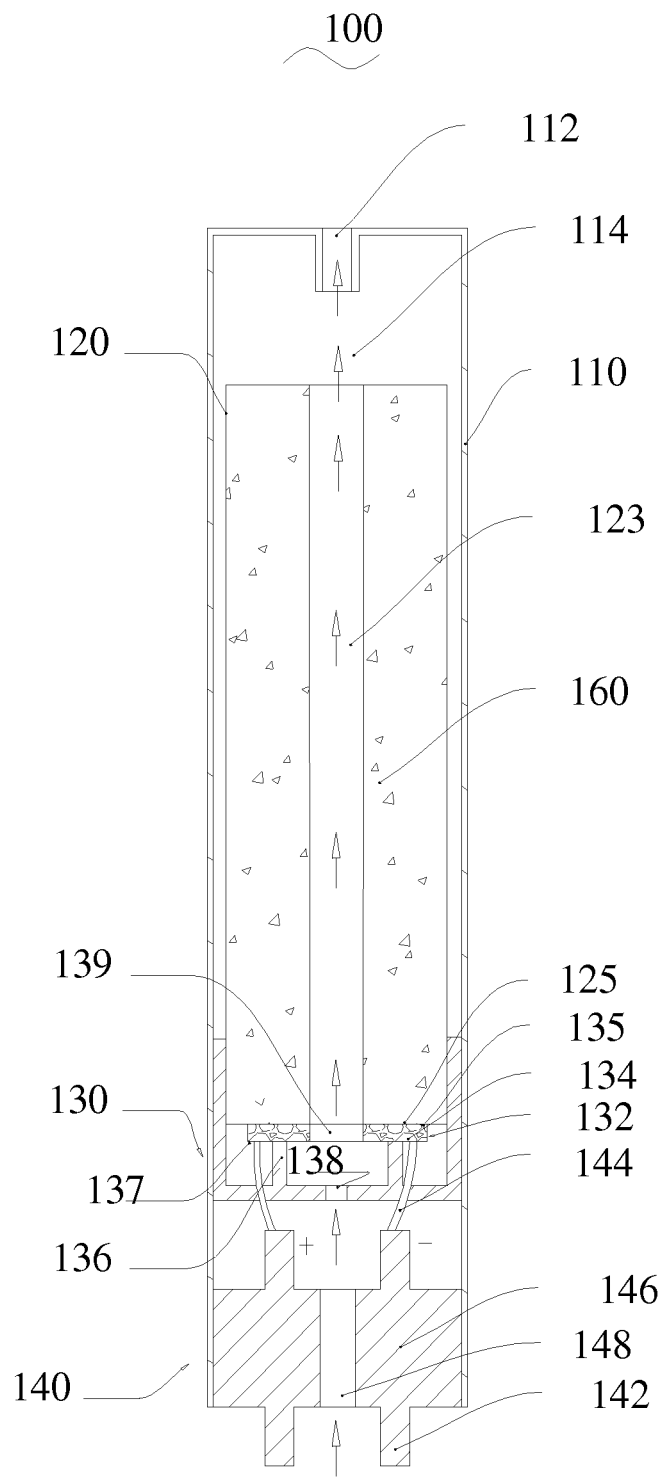
FIG. 3 is a cross-sectional view of the electronic cigarette according to a second embodiment.

Referring to FIG. 3, the electronic cigarette 100 of a second embodiment is similar to that of the first embodiment; the difference is that the liquid reservoir 120 is made of heat resistant and non-toxic sponge. The liquid 160 is absorbed and stored in the liquid reservoir 120. The bottom wall 125 of the liquid reservoir 120 is bonded to the upper wall 135 of the heating plate 132, the lower wall 137 of the heating plate 132 is in contact with the air in the chimney 114. The air in the chimney 114 is capable of blowing the lower wall 137 when flowing. Further, the heating plate 132 is made of foamed metal, which is a microporous plate with about 2000 to 3000 micropores per square centimeter. The micropores are penetrated through the upper wall 135 and the lower wall 137, the upper wall 135 of the heating plate 132 is directly bonded to the bottom wall 125 of the liquid reservoir 120 to form a face to face contact. The liquid 160 can be quickly absorbed by the heating plate 132 by capillary action with a suitable amount, and then uniformly distributed on the heating plate 132. The liquid 160 can be spread from the upper wall 135 to the lower wall 137, and heated by the heating plate 132 to form atomized particles; the atomized particles are transferred from the lower wall 137 to the air in the chimney 114.

In addition, referring to FIG. 3, the liquid reservoir 120 has a central tube 123, the heating plate 132 has a ventage 139. The central tube 123 and the ventage 139 cooperatively form a portion of the chimney 114. The air entered from the air inlet is freely passed through the chimney 114 and out from the air outlet 112 for the user to inhale. Since the pressure in the chimney 114 is smaller than that of the liquid reservoir 120, the liquid 160 is freely absorbed by the heating plate 132.

Although the subject matter has been described in language specific to structural features, it is to be understood that the subject matter defined in the appended claims is not necessarily limited to the specific features described above. Rather, the specific features described above are disclosed as example forms of implementing the claims. Numerous modifications and alternative arrangements can be devised without departing from the spirit and scope of the described technology.

What is claimed is:

1. An electronic cigarette, comprising:
    a housing having a chimney formed therein, the chimney further comprising an air space;
    a liquid reservoir received in the housing and positioned in proximity to the chimney, the liquid reservoir configured to hold a liquid;
    an atomizer assembly received in the housing and comprising a heating plate;
    the heating plate positioned in the air space and being spaced away from the liquid reservoir with an outer surface of the heating plate comprising a first side with an enlarged surface area that faces towards the liquid reservoir and an opposing second side with an enlarged surface area, both of the first and second sides being exposed in the air space and narrow sidewalls that extend between the first and second sides;
    a conductor that extends between the liquid reservoir and the heating plate and is configured to transfer the liquid from the liquid reservoir to the heating plate;
    the heating plate capable of absorbing the liquid, the outer surface of the heating plate is in contact with air in the chimney.

2. The electronic cigarette according to claim 1, wherein the heating plate defines a plurality of micropores thereon.

3. The electronic cigarette according to claim 2, wherein the micropores are penetrated through the heating plate; the air in the chimney is capable of blowing across the first and second surfaces of the heating plate.

4. The electronic cigarette according to claim 1, wherein the heating plate defines a ventage for air circulation.

5. The electronic cigarette according to claim 1, wherein the heating plate comprises a plate-shaped substrate and a heating film covered on a surface of the substrate.

6. The electronic cigarette according to claim 5, wherein the heating film is a PTC film or a conductive heating coating layer.

7. The electronic cigarette according to claim 1, wherein the heating plate comprises a plate-shaped substrate and a heater placed close to one side of the substrate.

8. The electronic cigarette according to claim 1, wherein the heating plate is made of foamed metal, foamed graphite or porous ceramic.

9. The electronic cigarette according to claim 1, wherein an air passage on an opposing side of the heating plate from the liquid reservoir is located in the center of the housing.

10. The electronic cigarette according to claim 1, wherein the chimney is located close to a side of the housing, at least a partial wall of the chimney is integrally formed with a wall of the liquid reservoir.

11. The electronic cigarette according to claim 1, wherein a side wall of the heating plate and a wall of the chimney defines an air space for air circulating therebetween.

12. The electronic cigarette according to claim 1, wherein the liquid reservoir is a liquid container located in the housing, the liquid container defines an outlet orifice allowing the liquid to flow out on an end thereof.

13. The electronic cigarette according to claim 1, wherein the atomizer assembly comprises an insulating supporter received in the housing; the heating plate is fixed to the insulating supporter.

14. An electronic cigarette, comprising:
    a housing that includes opposing first and second ends and sidewalls that extend between the ends and form an interior space;
    a liquid reservoir positioned in the interior space of the housing, the liquid reservoir including walls that form an interior space to contain a liquid;
    an air passage that extends through the housing and includes an inlet at the first end of the housing and an outlet at the second end of the housing, the air passage formed at least in part by the walls of the liquid reservoir;
    a heating plate with first and second sides each with enlarged surface areas and narrow sidewalls, the heating plate positioned in the air passage and being spaced away from the liquid reservoir with the first side facing towards the liquid reservoir, the heating plate comprising micropores to absorb the liquid;
    a conductor that extends between the liquid reservoir and the heating plate and is configured to transfer the liquid from the liquid reservoir to the heating plate;
    the heating plate being positioned in the air passage with the liquid that is atomized on the first and second surfaces of the heating plate being diffused to the air passage and moved out of the housing through the outlet.

15. The electronic cigarette according to claim 14, wherein the whole outer surface of the heating plate is exposed in the air passage.

* * * * *